(12) United States Patent
Bertheussen

(10) Patent No.: US 6,833,271 B2
(45) Date of Patent: Dec. 21, 2004

(54) SERUM-FREE CELL CULTURE MEDIA

(75) Inventor: Kjell Bertheussen, Tromso (NO)

(73) Assignee: Medi-Cult A/S, Copenhagen (DK)

(*) Notice: Subject to any disclaimer, the term of this patent is extended or adjusted under 35 U.S.C. 154(b) by 0 days.

(21) Appl. No.: 09/878,176

(22) Filed: Jun. 12, 2001

(65) Prior Publication Data

US 2002/0031825 A1 Mar. 14, 2002

Related U.S. Application Data

(63) Continuation-in-part of application No. 09/324,121, filed on Jun. 2, 1999, now abandoned, which is a continuation of application No. PCT/EP97/06721, filed on Dec. 1, 1997.

(30) Foreign Application Priority Data

Dec. 4, 1996 (GB) .............................. 9625175

(51) Int. Cl.[7] .................. C12N 5/06; C12N 5/08; C12N 5/00; C12N 5/02
(52) U.S. Cl. .................. 435/404; 435/325
(58) Field of Search ............... 435/404, 325, 435/434

(56) References Cited

U.S. PATENT DOCUMENTS

| | | | |
|---|---|---|---|
| 4,216,203 A | | 8/1980 | Johnston |
| 4,514,387 A | | 4/1985 | Wissler |
| 4,533,637 A | | 8/1985 | Yamane et al. |
| 4,582,826 A | * | 4/1986 | Inada ................ 514/182 |
| 4,657,866 A | | 4/1987 | Kumar |
| 4,687,744 A | * | 8/1987 | Kerwin et al. |
| 5,045,454 A | | 9/1991 | Bertheussen |
| 5,045,467 A | | 9/1991 | Bertheussen |
| 5,372,943 A | | 12/1994 | Inlow et al. |
| 5,378,612 A | | 1/1995 | Nakashima et al. |
| 5,413,928 A | | 5/1995 | Weathers et al. |
| 5,599,659 A | | 2/1997 | Brasile et al. |

FOREIGN PATENT DOCUMENTS

| | | |
|---|---|---|
| DE | 37 11 699 | 11/1988 |
| DE | 0 354 129 | 2/1990 |
| WO | 89/01027 | 2/1989 |
| WO | 89/06686 | 7/1989 |
| WO | 90/03429 | 4/1990 |
| WO | 92/22637 | 12/1992 |

OTHER PUBLICATIONS

Webster's Dictionary. 1984. p. 259.*
Patent Abstracts of Japan, XP–002065238 "Plant Tissue Cultering Method—Using Culture Medium Contg. One or More Sulphoxide(s), Poly–Hydric Alcohol(s), Organic Acids and Steroid(s)", Sep. 1998.
Dorner et al. "Increased Synthesis of Secreted Proteins Induces Expression of Clucose–Regulated Proteins in Butyrate–Treated Chinese Hamster Ovary Cells", The Journal of Biological Chemistry, 1989, pp. 20602–20607.
R. Ian Freshney, "Culture of Animal Cells A Manual of Basic Technique", 1994, pp 88.
Albert L. Lehninger, "Biochemistry the Molecular Basis of Cell Structure and Function", 1970, 513–516.
David Barnes, "Nutritional and Hormonal requirements of Mammalian Cells in Culture", Wld Rev. Nutr. Diet., vol. 45, 1985, pp. 167–197.
ATCC Cell Lines and dHybridomas, Catalogue, 8th Edition, 1994, pp. 515–516.

* cited by examiner

*Primary Examiner*—Vera Afremova
(74) *Attorney, Agent, or Firm*—Pillsbury Winthrop LLP

(57) ABSTRACT

Cell culture media containing a sterol such as cholesterol stabilized by surfactant rather than serum products or phospholspid micelles and containing soluble carboxylic acids as fatty acid precursors to satisfy lipid requirements are further enhanced by the presence of alcohols promoting cell growth.

6 Claims, 19 Drawing Sheets

No. of cells x10$^5$/flask (5 ml)

Type of cholesterol analogue

SERUM-FREE CELL CULTURE MEDIA

This is a Continuation-In-Part of National application Ser. No. 09/324,121 filed Jun. 2, 1999, now abandoned, which is a continuation of International Application No. PCT/EP97/06721 filed Dec. 1, 1997 which designated the U.S which claims priority from Great Britain application No. 9625175.6, filed Dec. 4, 1996.

The present invention relates to cell culture media and compositions for use in making such media.

Cell culture media are used for the culture of a wide range of cell types under varying circumstances and for varying purposes, which may or may not involve the division and multiplication of the cells. The term "cell culture medium" is used herein to refer to any medium in which cells are maintained in vitro in an active and viable state.

As is well understood in this art, the culture of cells requires the supply to the cells of the materials which they need for the maintenance of viability and, if desired, for the production of cell products and/or the multiplication of the cells. Whilst many of these materials may be supplied in purified or synthetic form, serum has traditionally been required for the supply of others. The simpler materials required by cells in culture may be formulated into a basal cell culture medium typically containing inorganic salts, amino acids, vitamins, and various other additives. A number of formulations of such basal media have been proposed. In such basal media without serum supplementation however, cells quickly die. Serum contains a number of biochemical entities that the cells need for survival in such basal media. Some of these entities protect the cells against toxic impurities in the basal media, some of which may be products of the cells themselves, and others serve to present iron and trace metals to the cells in a way the cells can use. The addition of serum can produce a well functioning medium for many different cell types, but serum brings with it severe disadvantages.

These have driven attempts to devise successful cell culture media that are serum-free. These disadvantages include the following:

serum is a non-physiological fluid for cells, due to many differences in composition compared to the interstitial tissue fluid and also when compared to plasma;

serum has an inflammatory and transforming effect on cells inducing hyperstimulation and other phenomena due to its content of products released from blood platelets and leukocytes;

antibodies and plasma factors produce strong or destructive interference in scientific experiments and in biotechnological production. For instance, the production of purified monoclonal antibodies is made much more difficult;

since the blood stream constitutes a transport system for nutrients and also for waste products, all kinds of waste products from the body's food intake and metabolism will be presented to the cultured cells, possibly with slaughter house contaminants;

serum is subjected to a heat treatment to inactivate lytic components which also has a denaturing effect on several serum proteins;

serum is not a reproducible and fixed material. Significant batch to batch variations interfere with the reproducibility of culture processes;

serum may contain known and unknown undesirable materials including viral or prion-type pathogens; and serum may be expensive and difficult to acquire.

Lastly, while serum-containing media have been especially successful for cells of mesodermal origin, cells originating from embryonic ectoderm or endoderm have proved most difficult to keep in good condition in serum-supplemented basal media. This is also true for gametes, both egg cells and sperm cells.

A major advance in the formulation of cell culture media eliminating the presence of serum was described by us in U.S. Pat. No. 5,045,454. There we described an additive to basal media comprising EDTA in combination with citrate buffer to complex iron and prevent its precipitation and aurintricarboxylic acid to present the iron effectively to the cells. The present invention provides a number of distinct and separately useful improvements to the media previously available, each of which is particularly useful by itself or in combination with one or more of the others in improving the media described in U.S. Pat. No. 5,045,454.

The inclusion of lipids in cell culture media is a long standing problem. Lipids which it is desired to include have a variety of differing functions. They include long chain fatty acids, fat soluble vitamins and sterols such as cholesterol. The direct addition of lipids is not practical because of their low solubility. Conventionally in serum containing media, the lipids are added to the medium in the serum, wherein the lipids are carried as soluble lipoproteins. In serum free media, lipids can be carried by albumen, but it is of course desirable to avoid the use of albumen also. A number of publications including 'Nutritional and Hormonal Requirements of Mammalian Cells in Culture' D. Barnes, Wld Rev. Nutr. Diet., vol. 45 pp 167–197 describe the provision of lipids in cell culture via the inclusion of liposomes formed using phospholipids such as are found in such sources as cod liver oil (WO-A-8901027 and others). For convenience, the cholesterol which is to be included in the medium may be added with the lipids in such liposomes.

Such methods involve the use of poorly characterised materials such as cod liver oil, serving as the source of the phospholipids needed for producing the liposomes or microemulsions needed. This again is an undesirable feature of such media. There remains a need for a more acceptable method of including cholesterol in the media.

U.S. Pat. No. 4,533,637 describes the formation of inclusion complexes between lipids and cyclodextrins. We have found that lipid fatty acids and other lipids complexed with cyclodextrins do not function well in cell culture—in part due to low stability in solution.

'Biochemistry-The Molecular Basis of Cell Structure and Function', Albert L. Lehninger, Worth Publishers Inc. 1970, p 513–514 discloses that acetic acid can be a metabolic precursor of longer chain fatty acids in an isolated supernatant fraction of the liver following centrifugal removal of mitochondria, but only in the presence of carbon dioxide or bicarbonate. A metabolic pathway through malonyl CoA formed from acetyl CoA is described.

U.S. Pat. No. 5,378,612 describes low-protein media in which Pluronic F-68 surfactant is used in combination with cyclodextrin. Butyric acid is added to enhance protein expression and lithium salts, including lithium acetate, are also added for this purpose. No growth promoting effect due to the addition of carboxylic acids and their salts is noted or intended however. The media described are unsuitable for producing cell growth. They allow a short period of protein production prior to eventual cell death. This method of operation is necessitated by the lack of an adequate protein free growth medium. Several other disclosures have also noted the protein expression enhancing effect of butyric acid without describing any cell growth promoting effect.

Ethanol has been used in preparing culture media for the purpose of dissolving fatty materials including cholesterol and other hydrophobic compounds when making a concentrate to be diluted in aqueous media at a later stage, e.g. in WO-A-9204988. Accordingly, ethanol has been present in some cell culture media in the past in small quantities carried over from its use as a solvent for lipids such as cholesterol. For instance, CMRL 1066 (a standard basal medium formulation—see "Culture of animal cells" R. I. Freshney, 3rd Edition, Willey-Liss), contains 16 mg/l ethanol for this reason. WO92/22637 describes solubilising cholesterol in ethanol, followed by the production of liposomes for addition to culture media. The quantities of ethanol present in the cell culture media through this route will however not have been adequate to provide a significant growth promoting effect as described hereafter according to the invention. Also, when ethanol is included in a serum supplemented medium, no growth promoting effect is seen.

We have now made a number of discoveries resulting in improved cell culture media that may be employed separately or in combinations of some or all of such improvements.

First, we have now found surprisingly that surfactant, e.g. a surfactant of the type known as PLURONIC F68 (PF68) can be used to the exclusion of protein agents to incorporate otherwise water insoluble lipids or lipid precursors such as cholesterol and/or other sterols into serum-free media. PLURONIC F68 is also known under the names POLOXAMER 188, POLOXALKOL and EXOCORPOL.

This enables the lipid requirement to be satisfied by a stable, synthetically produced, chemically pure material, whereas in media such as CMRL 1066, the cholesterol would precipitate out and in more recent media the cholesterol is not present in pure form but stabilised by proteins which are purified from natural sources and introduce problems of lack of reproducibility and potential contamination.

In a first aspect, the present invention provides a cell culture medium containing one or more synthetic lipids or lipid precursors, e.g. a sterol or a metabolically acceptable derivative thereof in solution stabilised by one or more surfactants and in the substantial absence of protein and of phospholipid.

The cell culture media of the invention are preferably growth media.

The sterol or derivative thereof may be one or more of cholesterol, campesterol, desmosterol, ergosterol (produced by yeast), fucosterol, β-sitosterol (produced by soya beans), stigmasterol, or a metabolically acceptable derivative thereof. It may be present as a said derivative which is an ester. Other metabolically acceptable derivatives may be used, i.e. derivatives which perform the role of such sterols in cell culture satisfactorily and without toxic effects. Suitably, the ester is an acetate. As further alternatives to cholesterol, other sterols including, other methyl cholesterols, various hydroxy-cholesterols, epi-cholesterol, cholesterol, and β-estradiol may be used.

Having regard to the superior results described below, the invention includes a cell culture medium containing a mixture of campesterol and β-sitosterol.

For use in all aspects of the invention, the sterol is preferably not a sterol produced by animals or is at least not a sterol produced by mammals. Sterols that are also produced by animals are preferably not used even if the actual source of the sterol used is non-mammalian. For instance one may use a plant sterol (being a sterol synthesised by plants but not by animals), a microbial sterol (being a sterol synthesised by a micro-organism (e.g. bacteria or yeast) but not by animals) or a non-natural sterol (i.e. a sterol made synthetically and not found in nature). Non-natural sterols include sterols produced by genetically engineered organisms and which are not found in nature but not sterols synthesised by any naturally occurring living organism.

Sterols that are synthesised by both plants and microorganisms (but not animals, or not mammals) are not included amongst the sterols which may advantageously be used in the various aspects of the invention.

Thus, preferred sterols for each aspect of the invention exclude cholesterol (however actually produced).

It is a surprising finding of the inventors that culture media according to the invention containing non-mammalian or non-animal sterol can be used successfully or even advantageously in the culture, especially growth culture, of animal (including mammalian) cells, such as human cells.

The preferred sterols (i.e. the non-animal sterols) may be used in combination with one another and may also be used in combination with one or more animal sterols (whether naturally or synthetically produced). For instance, the non-animal sterols may be used in combination with cholesterol.

Mixtures of non-animal sterols that may be used include stigmasterol and β-sitosterol, e.g. in a weight ratio of from 2:1 to 6:1.

There is further provided a cell culture medium containing cholesterol or another sterol having similar properties in cell culture solubilised by an α-hydro-w-hydroxypoly oxyethylene)poly(oxypropylene)poly(oxyethylene) block copolymer surfactant of the structure $HO(CH_2CH_2O)_a(CH(CH_3)-CH_2OH)_b(CH_2CH_2O)_cH$ where a is from 50 to 100, b is from 20 to 40 and c is from 50 to 100, with an average molecular weight of from 7,500 to 10,000 in the substantial absence of other cholesterol solubility stabilising agents, i.e. proteins such as serum components or albumen.

Preferably, a=75, b=30, and c=75 and said average molecular weight is about 8350.

More preferably, said surfactant is PLURONIC F68. Other surfactants, particularly non-ionic surfactants that do not interfere with the action of the cell culture medium may be included but preferably are absent, e.g. polyoxyethylene sorbitan monooleate type surfactants such as Tween 80.

However, it has been found that the natural surfactant cholic aid may in certain types of cell culture provide a growth stimulating effects. Accordingly, the invention includes a cell culture medium containing cholic acid.

Preferably, the culture medium contains from 0.05 to 20 mg/l of cholesterol, more preferably from 0.5 to 10 mg/l, for instance from 0.05 to 2 mg/l.

Preferably, the culture medium comprises from 20 to 300 mg/l of said surfactant, more preferably 50 to 200 mg/l, more preferably about 100 mg/l.

The cholesterol or other sterol and the surfactant may be prepared in a concentrated solution for addition to a basal medium to form a culture medium containing these materials in the required quantities. Such a concentrate is conveniently prepared by dissolving them in alcohol, preferably ethanol, and the addition of such a concentrate to a basal medium as described in detail hereafter can provide to the basal medium a quantity of alcohol sufficient to provide a cell growth promoting effect according to an alternative aspect of the invention.

The cell culture medium may further contain a soluble carboxylic acid or metabolically acceptable derivative thereof as a metabolic precursor of lipid fatty acids. Said carboxylic acid is preferably a $C_2$ to $C_7$ carboxylic acid which is preferably saturated and preferably contains one carboxylic acid group. The carboxylic acid may be added as the acid as such or in the form of a metabolically acceptable salt or other derivative such as an ester. Preferably, said carboxylic acid or derivative is present at a concentration of from 10 $\mu$M to 10 mM, more preferably from 50 $\mu$M to 1 mM, e.g. from 100 to 300 $\mu$M, most preferably at about 100 $\mu$M.

In a further aspect, the invention provides a cell culture medium containing an alcohol capable of promoting cell growth at an effective growth promoting concentration of at least 0.01% vol/vol acting as a cell growth promoting agent.

Preferably, the said alcohol concentration is from 0.01% to 0.25% vol/vol, more preferably from 0.075% to 0.2% vol/vol, for instance from 0.1% to 0.15% vol/vol.

Said alcohol may be a $C_1$ to $C_4$ mono-alcohol or diol. Suitable alcohols include methanol, ethanol, propanol, butanol, ethylene glycol, propylene glycol or glycerol but ethanol is most preferred. Preferably the alcohol concentration is at least 0.01% to 0.25% vol/vol, e.g. from 0.075% to 0.2% vol/vol, more preferably from 0.1% to 0.15% vol/vol (1% ethanol vol/vol=7.9 g/l).

The invention includes in this aspect the use of an alcohol, especially ethanol to promote cell growth in culture.

As mentioned above cholesterol is included in some cell culture media to provide lipid, often in combination with other lipids such as lecithin, sphingomyelin, fat soluble vitamins (A, D, E and K), phosphatidylcholine, phosphatidylethanolamine, phosphatidylinositol, dipalmitoyl phosphatidic acid and fatty acids. The incorporation of these hydrophobic materials poses problems. This has been addressed in the past by the use of complex lipoproteins, cyclodextrin or lipid micelles maintained by albumen to stabilise the cholesterol.

A further difficulty in preparing satisfactory serum-free media in the past has related to the incorporation of fatty acids. These pose a solubility problem and in addition are chemically unstable, being subject to oxidation. We have surprisingly found that soluble carboxylic acids and their derivatives such as salts and esters can be utilised in cell culture for the synthesis of fatty acids by cells, removing the need to include fatty acids in the culture medium itself. Certain basal media formulations include one or more fatty acids such as linoleic acid. However, in these formulations the linoleic acid is not present in a useful form. It will precipitate at once when the medium is made ready for use. It is therefore necessary in practice to add lipid solubilising materials such as serum, albumen or liposomes to make the media acceptable to the cells. Accordingly, according to a further aspect of the invention there is now provided a growth medium for cell culture comprising a soluble carboxylic acid or metabolically acceptable derivative thereof for providing a metabolic precursor of lipid fatty acids and/or for increasing cell growth rate. Suitable carboxylic acids and their derivatives are described above.

Preferably, the concentration of the soluble carboxylic acid or salt in the culture medium is given above.

The medium may comprise polyvinylpyrrolidone such as PVP-10, molecular weight 10,000. Suitably this is present at a concentration of from 25 to 10,000 mg/l, more preferably 100 to 500 mg/l, e.g. about 250 mg/l.

The culture medium may in addition contain all or any of the ingredients in the proportions or amounts disclosed in U.S. Pat. No. 5,045,454 for use in that invention.

As disclosed there, the medium preferably comprises one or more chelators preventing precipitation of iron at culture temperatures, typically 37° C. The most preferred chelators are EDTA (ethylenediaminetetraacetic acid) and citrate buffer. Preferably the molar ratio of citrate buffer to EDTA is at least 3:1 citrate buffer: SDTA by molar concentration, more preferably about 10:1 citrate buffer: SDTA, where citrate buffer represents the sum of citric acid and citrate.

Iron is preferably supplied in the medium as the metal chelate complex defined as Fe-EDTA together with citrate buffer. More particularly, there may be provided about 2.4 to 3.6 $\mu$M Fe-EDTA and about 0.8 to 1.2 $\mu$M $Na_2$(or $K_2$) EDTA with about 12 to 18 $\mu$M citric acid and about 20 to 30 $\mu$M $Na_3$ Citrate. Other biocompatible chelating agents may be used.

An agent for presenting iron to the cells is preferably provided which preferably is aurintricarboxylic acid. This is preferably present at a concentration of from 0.1 to 10 $\mu$M, more preferably from 2.4 to 3.6 $\mu$M, e.g. 3 $\mu$M.

The pH of the medium may be between about 7.0 and 7.8, most preferably about 7.4 but the optimum may vary according to the nature of the cells in culture.

The culture medium is preferably serum-free and also protein-free except that it may be advantageous to add a small quantity of insulin, as described in U.S. Pat. No. 5,045,454.

Media containing insulin at the appropriate concentration for its use may still be regarded as substantially protein free.

Analogous to the methods described there, the culture media according to the various aspects of the present invention may be prepared by making up one of a number of standard or modified basal media and adding to it the additives disclosed in U.S. Pat. No. 5,045,454 from one or more concentrate solutions and the further additives required by the present invention from one or more further concentrates.

The basal media may be any of those known in the art including Eagle's MEM, Dulbecco's modified Eagle's MEM, Ham's F10/F12, CMRL, RPMI 1640, 199, L15, Fischer's or Waymouth's MB 752/1 (see Ref. 1). Preferably however, the basal medium is RPMI 1640. RPMI-X (a modified RPMI 1640 containing 20 mM HEPES and pyruvate) is preferred for the culture of cells of the leukocyte and reticulo-endothelial lineages, including lymphocyte hybridomas, while DME/F12 is preferred for use for other types of cells.

The recommended concentration of bicarbonate is 2.2 g/l and antibiotics such as penicillin or streptomycin should preferably not exceed 50 U/ml and 50 $\mu$g/ml respectively.

To such basal media may be added an appropriate amount of a "SSR2" as described in U.S. Pat. No. 5,045,454, i.e. a solution containing EDTA, citrate, iron and aurintricarboxylic acid as well as optionally PLURONIC F68, e.g. a "solution A" (U.S. Pat. No. 5,045,454, Col. 5) containing 20 mg/ml PLURONIC F68, about 4 mM EDTA, about 3 mM Fe, about 40 mM sodium citrate/citric acid, about 3 mM aurintricarboxylic acid and optionally about 1% trace elements. These amounts are suitable for a 1000× formulation, i.e. a solution containing 1000 times the concentration of each ingredient desired in the final solution and which is therefore intended to be diluted with 1000 parts of the basal culture medium. The trace elements may comprise Mn (about 1 $\mu$M), Cr (about 1 $\mu$M), Zn (about 0.1 $\mu$M), Ni (about 0.2 $\mu$M), Co (about 0.2 $\mu$M), Cu (about 20 $\mu$M), Al (about 2 $\mu$M) and Se (about 10 $\mu$M).

The basal culture medium may be further supplemented with an appropriate quantity of a further concentrate solution of the kind referred to as "Solution B" in U.S. Pat. No. 5,045,454 comprising about 0.5 mg/ml insulin (1000×).

Having regard to the above, the invention includes an additive for addition to a basal cell culture medium to form a serum-free cell culture medium, comprising:

an alcohol a sterol or metabolically acceptable derivative thereof, and a soluble carboxylic acid.

The invention further includes an additive for addition to a basal cell culture medium to form a serum-free cell culture medium, comprising equal volumes of 96% ethanol and water and 100 g/l Pluronic F68.

To put into effect the various aspects of the present invention, the resulting supplemented basal medium may be further modified by the addition of an appropriate quantity of a further concentrate comprising cholesterol in ethanol or methanol solution, optionally also containing acetic acid. Other ingredients that may be included here are PVP 10 and ethanolamine.

A suitable composition for such a 1000× "Solution Cx" will be:

ethanol 96% 1 liter cholesterol (cell culture tested) 2 g (e.g. Sigma C-7402 C-3405)

PVP-10 250 g (plant cell tested) e.g. Sigma P-2307 concentrated acetic acid 6 ml (to 100 mM)

1.2 ml concentrated solution of ethanolamine (to 20 mM)

pH of concentrate 6.5

Depending on its intended use, the cell culture medium may be further supplemented using a concentrate "Solution Dx" containing ethanol and PVP-10, e.g. a 1000× solution containing:

ethanol 96% 500 ml water 500 ml

PLURONIC F68 100 g (Serva 35724 or Sigma P-1300)

We have found that certain commercially available basal culture media are capable of being improved by an iron conditioning process which results in a growth stimulating effect that may be due to the chemical reduction of organic molecules and the absorption of toxic contaminants into a fresh precipitate of iron hydroxide produced by the process.

Accordingly, the invention includes in a further aspect a method of conditioning a basal culture medium for increased cell growth comprising in water used for making up a powder basal cell culture medium acidified ferrous sulphate and precipitating iron hydroxide from the made up powder by the addition of bicarbonate.

The conditioned basal medium so produced should be sterile filtered to remove the precipitate prior to the addition of solutions A, B, Cx and, if required, Dx described above, if the other aspects of the invention are to be used also.

A 1000× solution for use in said conditioning step may be prepared by dissolving $FeSO_4$ to 50 mM in 100 ml water plus 0.2 ml 2.5 M $H_2SO_4$ and diluting by 10× in water.

Commercially available media powders produced by Sigma and Imperial benefit from this conditioning process. Generally speaking, the conditioning process will not be appropriate for conventional IVF media and Ham's media, HF 10/12, MCDB media and DME/F 12 contain relatively high amounts of unstable ferrous sulphate and should not be treated in this way. The conditioning process should therefore in general be applied to basal media that will as a result produce better cell growth.

BRIEF DESCRIPTION OF THE DRAWINGS

The invention will be further illustrated by the following description of preferred features and illustrative examples thereof with reference to the accompanying drawings in which:

FIG. 1 shows the growth promoting effects of ethanol in cell culture as found in Example 1a;

Figure 1:
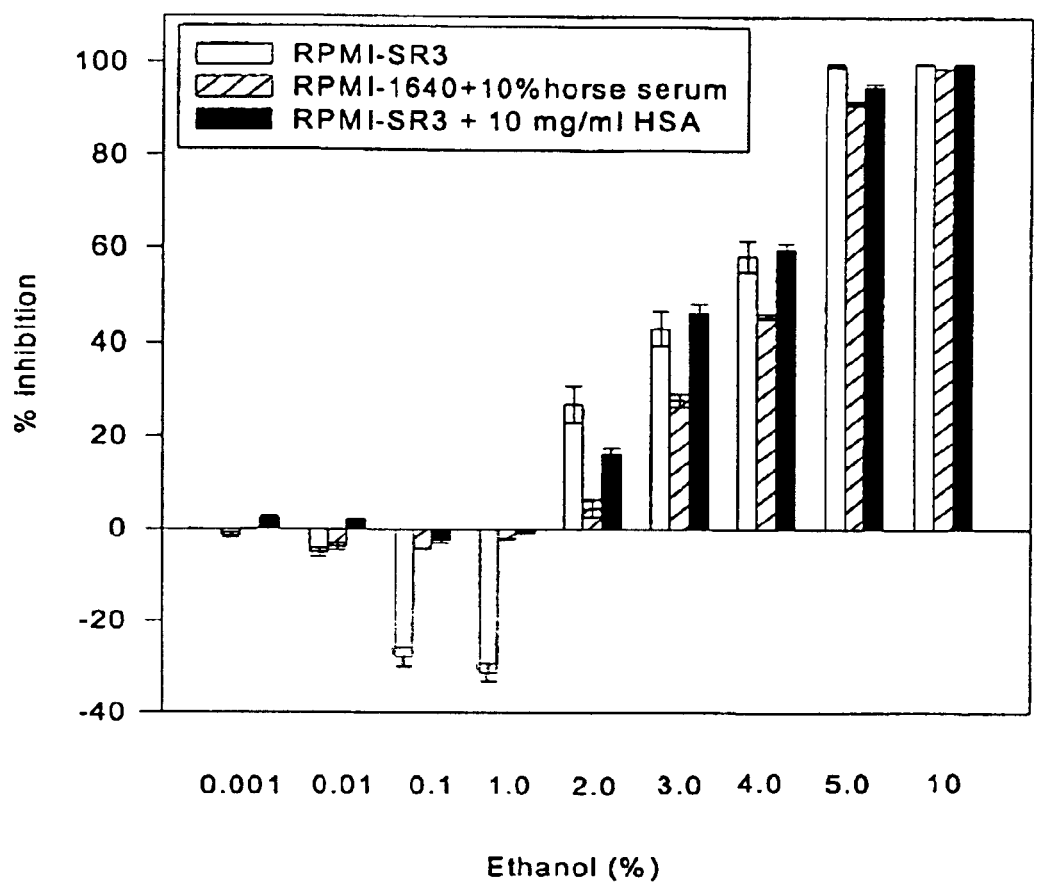

Cultivation of adherent cells or of lymphocytes, which in culture depend on cytokines produced by adherent cells, is preferably carried out on gelatin and fibronectin coated TC plastics. When TC plastics pre-coated with gelatin is treated with active serum, e.g. fetal bovine serum, fibronectin selectively binds to the gelatin surface, and following washing this makes the optimum substrate for culture using serum free media.

Several transformed adherent cell lines can be cultured in suspension in for instance DME/F12 supplemented by solutions A, B, Cx and Dx, for instance CHO—K1, MDBK, HELA S3, and some WEHI lines. The cells tend to grow as micro aggregates, and one should select a type of TC plastics with minimum adherent properties as weak adherence is growth inhibiting compared to either no adherence or strong adherence. Similar low adherence plastics should be used for culturing lymphocyte hybridomas in RPMI-x supplemented with solutions A, B, Cx, and Dx. The growth curves shown in the Figures were obtained using Nunc TC flasks.

Advantages of the preferred cell culture media of the invention in its various aspects include the following. The presence of PVP-10 is advantageous in that it binds low-molecular weight organic compounds, for example phenolic compounds, i.e. it exhibits albumen like properties. It therefore detoxifies waste products in high-density cell cultures and thereby increases the productivity of the cell culture by facilitating high cell density.

Cholesterol is kept in solution in the final medium at storage temperature (4° C.) by the surfactant PLURONIC F68 that comes from solutions A and Dx and by the contribution of ethanol from solution Cx. Cholesterol becomes less soluble at cultivation temperatures (37° C.) and will gradually precipitate in cell cultures unless the cell density is at least $10^5$ cells/ml, which is in practice always the case in cell culture for biotechnological production purposes. Thus the need to present cholesterol in a soluble state is met without including lipoproteins and other undesirable complex forming materials.

The balance of the amount of cholesterol and PLURONIC F68 may be adjusted to suit the cells being cultured. The use of solutions A, B and Cx leads to a high surface tension which promotes attachment of adherent cells to a solid surface. The high surface tension is made possible by a high concentration of cholesterol in relation to the surfactant. As a result the cholesterol is less stable than when solution Dx is added also, but at the same time ensures high surface tension during the whole of the cultivation period. A small precipitate of cholesterol may possibly cover the cell monolayer at first, but this will be rapidly absorbed during the first 24 hours of cultivation.

By including solution Dx also, a lower surface tension is produced by changing the ratio between cholesterol and PLURONIC F68. The resulting surface tension favours the cultivation of cells in suspension.

Both PVP and PLURONIC F68 increase the viscosity of the medium and provide mechanical protection for the cells.

All the components of the system are of a molecular weight of not more than 10,000, facilitating the separation of the medium from cellular products.

No proteins or peptides are included except for a low concentration of insulin and no other products of animal or vegetable origin are present so that there is a high degree of reproducibility and stability.

Figure 2:
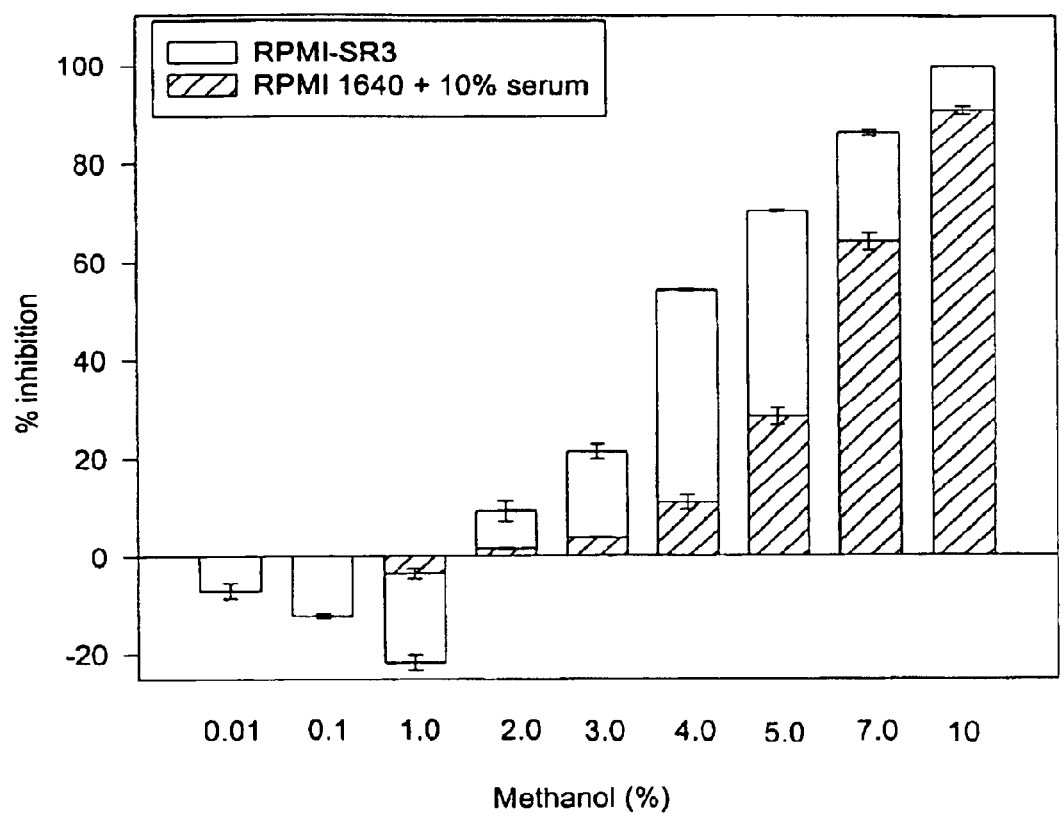
FIG. 2 shows the growth promoting effects of methanol as found in Example 1b.

EXAMPLE 1
The Growth Promoting Effect of Alcohols a) Hybridoma cells were cultured in RPMI 1640 supplemented with solutions A and B, described above plus 20 mM ethanolamine (referred to as RPMI-SR3), and by way of comparison in the same medium further supplemented with 10 mg/ml albumen (5% by vol.) or in RPMI 1640 supplemented with 10% v/v horse serum. The results are shown in FIG. 1. It can be seen that in RPMI-SR3 concentrations of ethanol of up to 1.0% by vol result in negative inhibition (i.e. promotion) of cell growth but that this effect is not apparent when the protein or serum supplemented media are used.

b) The above was repeated using methanol in place of ethanol with similar results, illustrated in FIG. 2.

In the following further examples growth curves are compared for cells cultured in media according to the invention and in media according to the prior art. Both cell culture in suspension and the culture of adherent cells are illustrated. A variety of transformed cells have been cultured in the media of the invention. Transformed cells are cells which are genetically modified, in a similar way to cancer cells, in that their growth is continuous and unregulated, i.e. the growth is independent of the presence of so-called cytokines (peptides that act as specific and regulatory growth factors). In general, transformed cell lines will grow in protein free media of the invention approximately as efficiently as in media containing 10% serum. EBV transformed B lymphocytes however may require some cytokines in the medium. As the following examples demonstrate, most hybridomas will grow at a somewhat reduced rate in these media compared to those containing serum, but production of antibody is nonetheless as good as with serum if not better. If the quality of the batch of serum is not optimum, the growth may be below that obtained with media according to the invention.

In these examples a combination of solutions A, B and Cx as described above is referred to as SSR3x and, when further supplemented with solution Dx described above, as SSR4x.

EXAMPLE 2
Growth of BHK-21 Cells in Serum Free Medium

Figure 3:
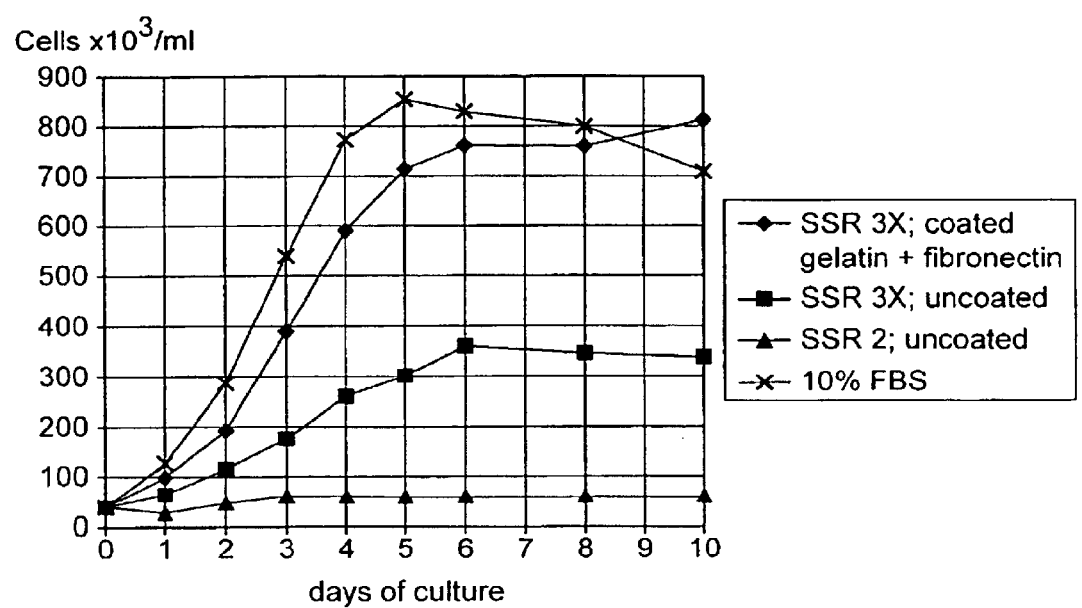
FIGS. 3 to 7 show cell growth measurements reported in Examples 2 to 6 respectively.

BHK-21 hamster kidney fibroblast cells (ATCC CCL10) were adapted to culture by two months culturing in DME/F12+SSR 3x medium of the invention. The cells were cultured as an adherent monolayer in 25 cm$^2$ Falcon T-flasks containing 7 ml medium, without changes of the medium at a seeding density of 40×10$^3$ cells/ml. Cell numbers after up to 10 days (counting only viable adherent cells) are shown in FIG. 3. Comparative culture under comparable conditions was performed using the same medium and either gelatin and fibronectin coated flasks or uncoated flasks and also using the basal medium modified with only solutions A and B (SSR 2), as in U.S. Pat. No. 5,045,454, with uncoated flasks. All these are compared with the use of the basal medium supplemented with 10% fetal bovine serum.

It was found that the morphology of the cells was superior in the SSR 3x containing medium compared to the serum containing medium. When the culture reaches confluence, the cells start detaching from the surface and will float in the medium as large aggregates or sheets. In the serum free medium, the cells remain alive for a long period in this state but in serum supplemented medium the cells start to die on reaching confluence.

From the figure it can be seen that SSR 3x promotes adhesion, compared to SSR 2.

EXAMPLE 3
Culture of Vero Cells

Figure 4:
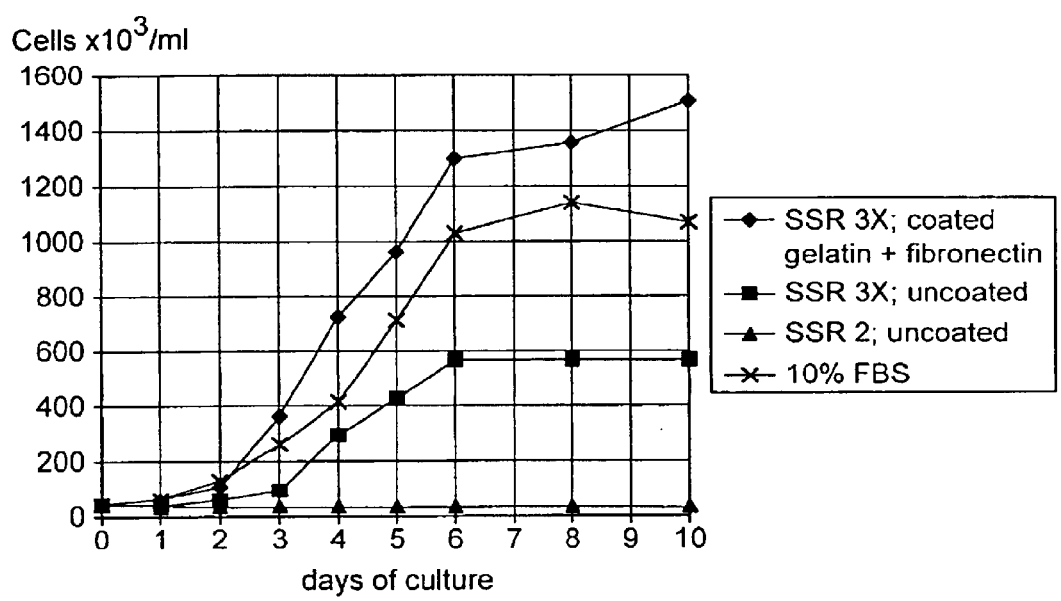

Vero (monkey kidney fibroblast) cells ATCC CCL 81 as typically used in viral vaccine production. Comparative cultures were performed as in Example 2. Results are shown in FIG. 4.

Growth in the serum free medium of the invention was superior to that in serum containing medium and growth was seen even on uncoated plates on which no growth was produced using SSR 2.

EXAMPLE 4
Growth of WEHI Cells

Figure 5:
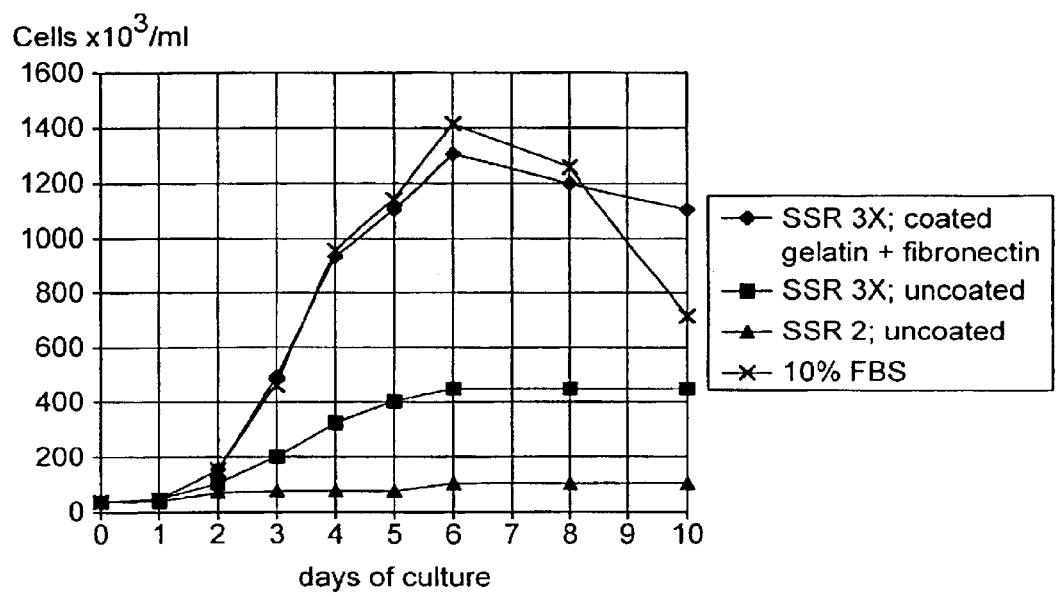

WEHI 164 mouse fibrosarcoma cells ATCC CRL 1751 were cultured as an adherent monolayer in 25 cm$^2$ Falcon T-flasks containing 7 ml medium, without changes of the medium at a seeding density of 40×10$^3$ cells/ml. Cell numbers after up to 10 days (counting only viable adherent cells) are shown in FIG. 5. It was found that the morphology of the cells was superior in the SSR 3x containing medium compared to the serum containing medium. When the culture reaches confluence, the cells start detaching from the surface and will float in the medium as large aggregates or sheets. In the serum free medium, the cells remain alive for a long period in this state but in serum supplemented medium the cells start to die on reaching confluence.

From the figure it can be seen that SSR 3x promotes adhesion, compared to SSR 2.

EXAMPLE 5
Growth of ECV 304 Cells

Figure 6:
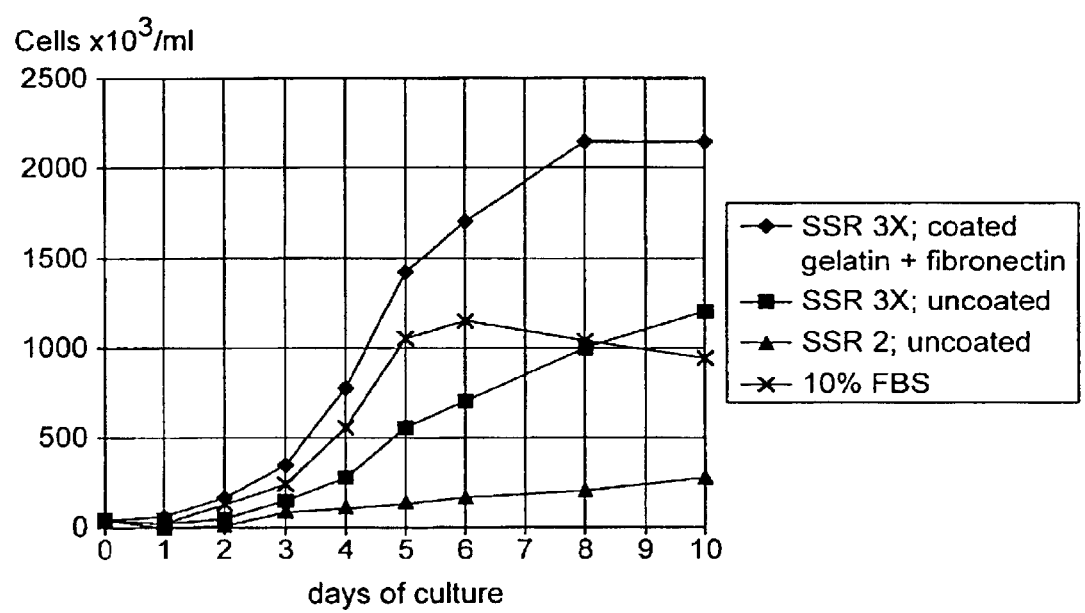

ECV 304 human endothelium umbilical cord cells ATCC CCL 1998 were adapted to culture by two weeks culturing in DME/F12+SSR 3x medium of the invention. The cells were cultured as an adherent monolayer in 25 cm$^2$ Falcon T-flasks containing 7 ml medium, without changes of the medium at a seeding density of 40×10$^3$ cells/ml. Cell numbers after up to 10 days (counting only viable adherent cells) are shown in FIG. 6.

EXAMPLE 6
Growth of Hybridoma Cells in Suspension

Figure 7:
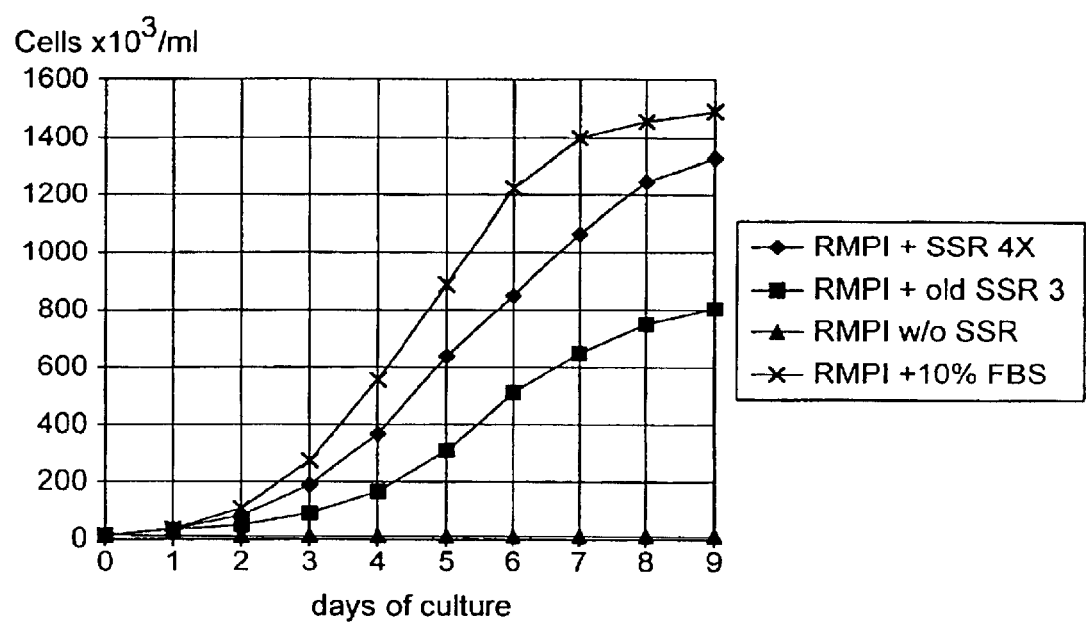

Mouse hybridoma H3 (IgM—Id$^3$) adapted were adapted by culture for four weeks in RPMI-X supplemented by SSR 4x. The growth of the cells in suspension culture was then studied over a 9 day period in 25 cm$^2$ Corning T-flasks containing 7 ml medium, without change of medium. The seeding density was 10×10$^3$ cells/ml. Cell numbers after up to 9 days (counting only viable cells) were as shown in FIG. 7.

Improved morphology and viability were observed using medium supplement SSR 4x compared to SSR 3. In cultures of high density, cell viability was 90% using SSR 4x but only 50% using SSR 3. Hybridoma cells will in general not grow in basal medium without supplementation.

EXAMPLE 7
Antibody Production

A number of different hybridoma cell lines were cultured in RMPI-X supplemented with SSR-4x or with serum as control.

All were all mouse hybrids using two myeloma cell lines 2/0, P3X63.Ag8 as fusion partners. The cell lines were chosen to challenge the properties of the media in different ways, some good antibody producers and some poor ones being included. Likewise, some cells had good growth properties and some poor. All hybridomas were seeded at $10^4$ cells/ml in three different media namely RPMI-X supplemented with SSR 4×, RPMI-I (a proprietary serum free medium) and in serum supplemented medium.

The growth rate in the serum containing medium was generally about 25% higher than in the serum free media, but antibody production in the SSR 4× supplemented medium was for 8 of the 9 hybridomas from 1 to 2.7 times higher than in the serum supplemented medium.

Supernatants from SSR 4× supplemented cultures and from serum supplemented cultures have been purified on a Protein A column. Gel electrophoresis of the purified product showed several extra bands in the case of the serum supplemented culture due to the presence of serum protein that had co-bound with the immunoglobulin of interest and had co-eluted from the column.

EXAMPLE 8
Testing of Sterols Other than Cholesterol

To demonstrate that the invention is applicable using sterols other than cholesterol, cell growth and cell morphology were examined in media containing alternative sterols. The following cell types were used:

| | Transformed adherent cells | |
|---|---|---|
| Vero | ATCC CCL 81 | Monkey kidney fibroblast |
| CHO-K1 | ATCC CCL 61 | Chinese hamster ovary epithelium |
| | Transformed cells growing in suspension | |
| 1E6 | ECACC 86112001 | Mouse hybridoma - fusion Balb/c with $P_3U_1$ myeloma |

The basal media used were DME/F12 for adherent cells, and RPMI-X for suspension cells. The basal media were supplemented by SSR2 described above, i.e. a solution containing 20 mg/ml PLURONIC F68, about 4 mM EDTA, about 3 mM Fe, about 40 mM sodium citrate/citric acid, about 3 mM aurintricarboxylic acid and about 1% trace elements. This was further supplemented with PEG (Polyethylene Glycol, MW 8000) in all test media except those of Example 10 to improve the basic viability of the cultured cells. For hybridoma cells, this was still further supplemented by ethanolamine at 20 $\mu$M. Each culture was run in duplicate. As a control, cholesterol was also used, but in this case the basal medium was supplemented by 'Solution Cx' or 'Solution Dx' described above, as appropriate to the cell type. The negative controls referred to below were in each case a cell culture containing no test substance (sterol).

Cells were cultivated through 2 passages for adherent cells, and 3 passages for the hybridoma line having regard to the greater difficulty of morphological scoring in suspension cultures, this being compensated by the longer culture period. All cultures of the same experiment were subcultured using an identical split ratio, for example 1:10; this ratio being adjusted in the individual experiments to suit the growth rate of the positive control (see above).

In principle then, slower growing cultures become more diluted for each passage, and the final (total) result provides a better differentiation of the cultures and a more safe final reading of cell number and morphology.

40 000 cells per ml medium were initially seeded in T-flasks (total 5 ml medium), and following a culture period of 4–6 days, the positive control reached a state of confluence. Then adherent cells were trypsinized and subcultured further for the second passage—followed by counting the number of cells when confluent for the second time.

Hybridoma cells, growing in suspension, were simply diluted in medium for each new passage.

Counting of all kinds of cells were generally performed using a standard Bürker chamber, and viability determined by Trypan Blue exclusion (only viable cells were counted). In some experiments, where feasible, cells were counted directly in the microscope viewing field using a calibrated grid. In addition, the quality of the cultured cells (mainly for adherent cells) was judged by phase contrast microscopy of living cells, and a certain morphological index was then assigned to each culture—ranging from zero (no viable cells seen in the culture) up to a maximum of 100 (the maximum quality possible, normally as seen in adherent cell cultures containing DME/F12 with 'Solution C'). The morphological index is mainly based on three properties: single cell morphology, number of cells, and the degree of uniform distribution of cells around the culture surface ('cellular behaviour').

Tests were conducted using the following analogues of cholesterol which were thought to be functional analogues of cholesterol for cell culture in being precursors of lipids synthesized by cultured cells which in the case of adherent cells maintain high surface tension facilitating hydrophobic attachment of cells to plastics surfaces. These compounds are thought to play a similar physiological role to cholesterol in plants or animals.

The tested compounds may be divided into various groups as follows:

those which are insoluble in water and give rise to high surface tension in the medium, i.e.:

| | |
|---|---|
| C 5157 | Campesterol |
| C 3045 | Cholesterol |
| D 6513 | Desmosterol |
| E 6510 | Ergosterol |
| F 5379 | Fucosterol |
| S 1270 | β-sitosterol 95% synth. |
| S 5753 | β-sitosterol 60% |
| S 6126 | Stigmasterol | the acetate esters of these compounds which are very slightly soluble in water but also contribute to producing a high surface tension, i.e.

| | |
|---|---|
| C 9329 | Cholesteryl Acetate |
| S 2265 | β-sitosteryl Acetate |
| S 6251 | Stigmasteryl Acetate | various products of cholesterol metabolism which are also insoluble in water and which give rise to high surface tension in the medium i.e.

| | |
|---|---|
| D 4429 | 7-dehydrocholesterol |
| D 6128 | Dihydrocholesterol (Cholestanol) |
| L 5768 | Lanosterol 97% |
| L 1504 | Lanosterol 50–60% | biologically active compounds (hormones, vitamins) which are somewhat soluble or insoluble in water but do not affect the surface tension of the medium i.e.

| E 9007 | Ergocalciferol |
|---|---|
| E 2758 | β-estradiol | and an example of a detergent (bile salt) which is a product of cholesterol metabolism which is very soluble in water and produces low surface tension i.e.

| C 9282 | Cholic acid |
|---|---|

The reference numbers quoted above are from the Sigma Catalogue. When the purity is less than 95%, the remainder is given as a mixture of closely related compounds by the manufacturer. For instance β-sitosterol 60% contains to 40% a mixture of mainly campesterol and dihydrobrassicasterol. Lanosterol 50–60% contains to 40–50% mainly dihydrolanosterol.

Figure 8:
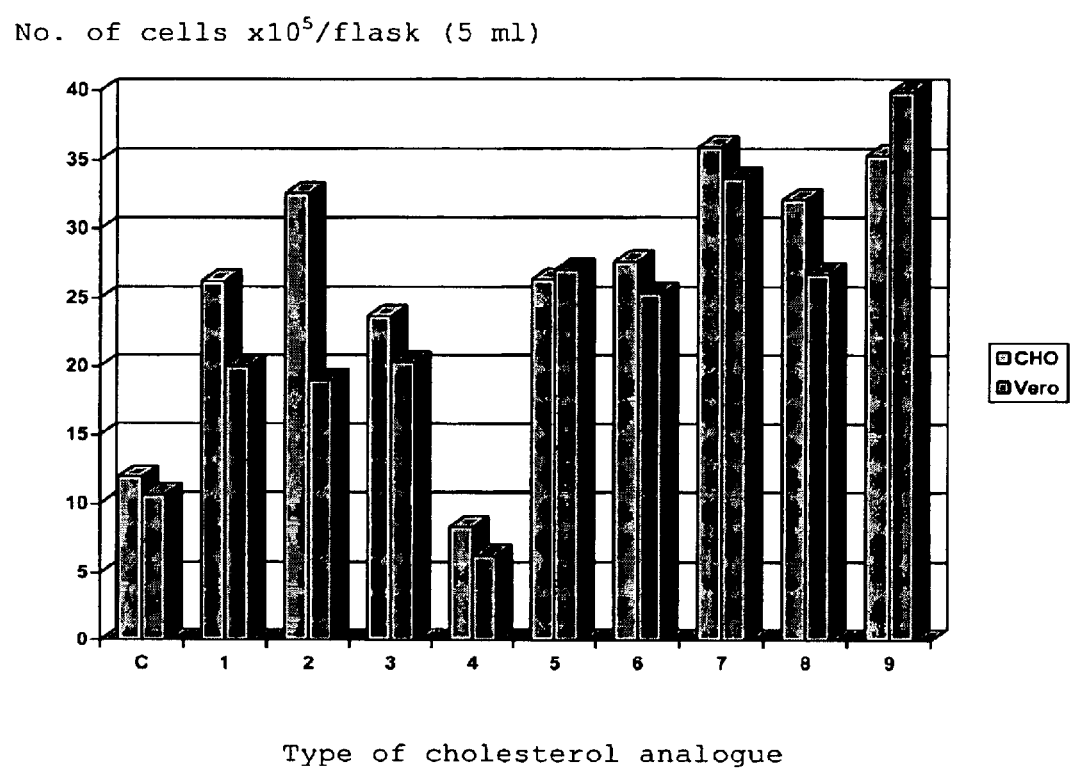
FIGS. 8 to 13 show results obtained in Example 8.
Figure 9:
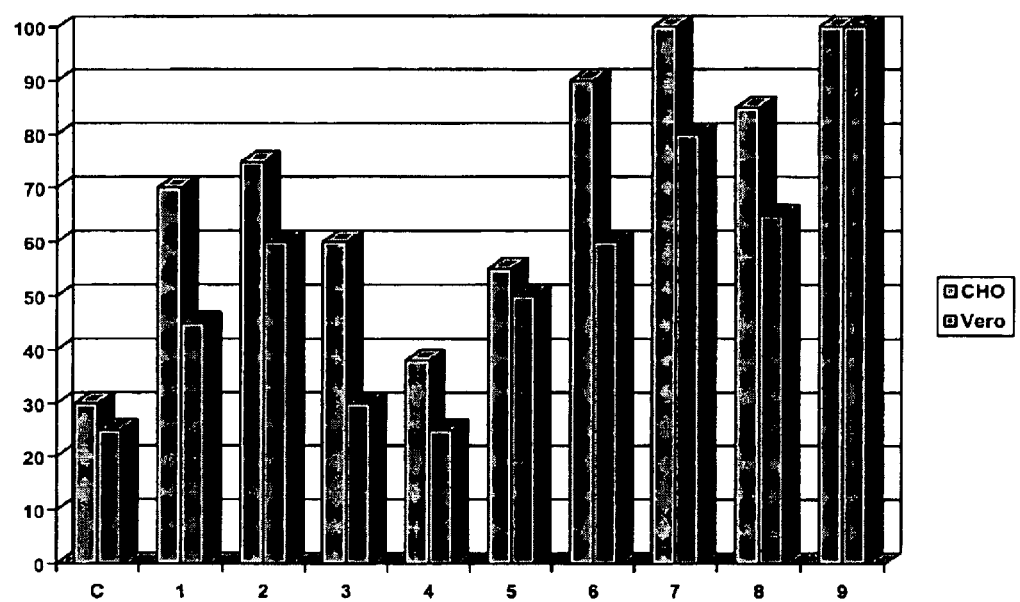
Figure 10:
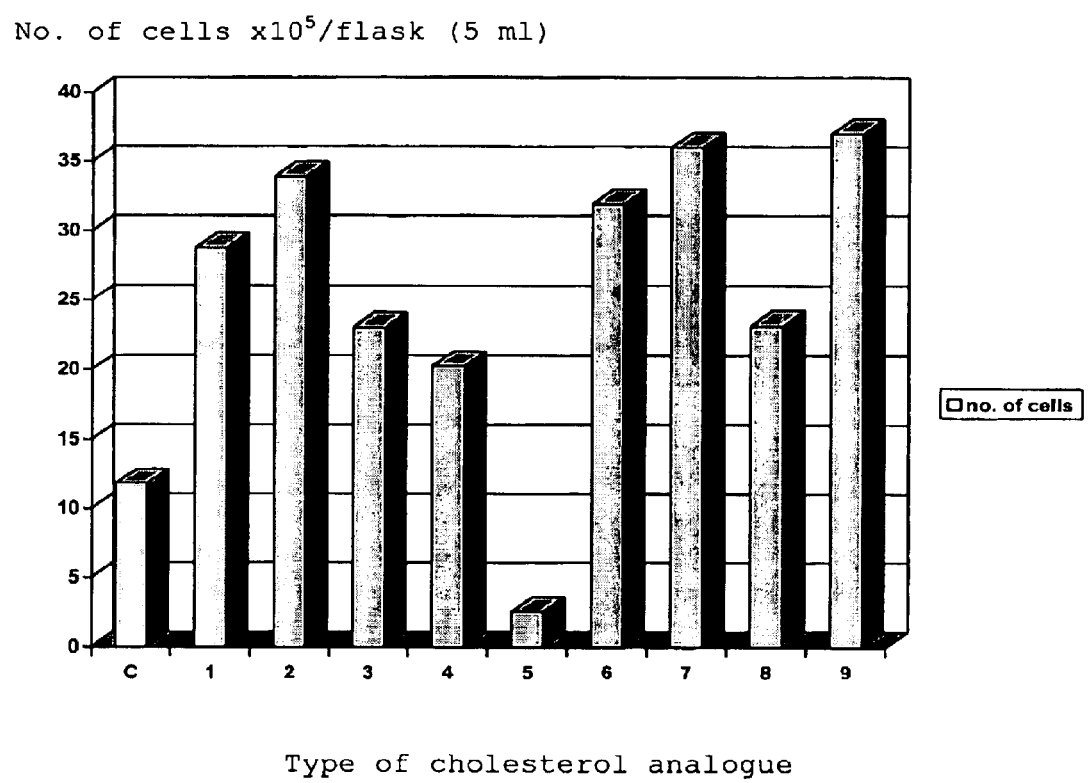

The results are shown in FIGS. 8 to 13. In FIGS. 8 to 10, the legend to the type of cholesterol analogue is as follows:

| 1 Cholesterol | 6 β-sitosterol 95% synth. |
|---|---|
| 2 Campesterol | 7 β-sitosterol 60% |
| 3 Desmosterol | 8 Stigmasterol |
| 4 Ergosterol | 9 mix 2 + 6 = 40:60 |
| 5 Fucosterol | C negative control |

The test concentration: 2 μg/ml, except Desmosterol: 1 μg/ml.
n.d. = not done.

Figure 11:
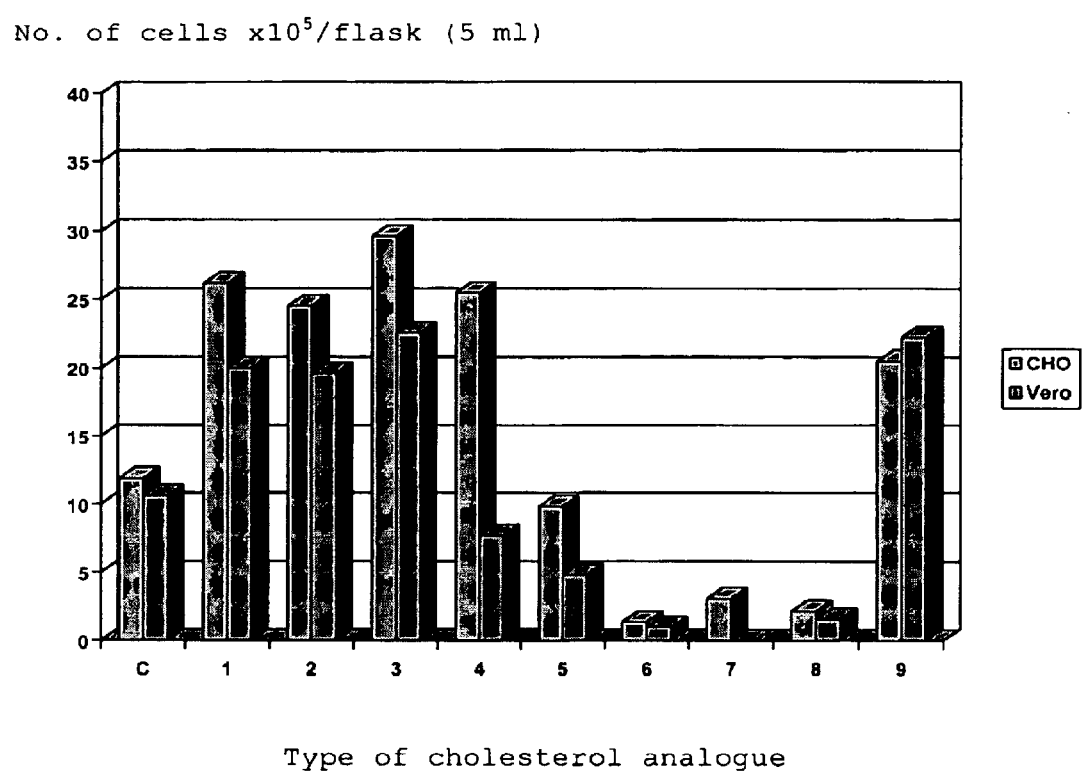
Figure 12:
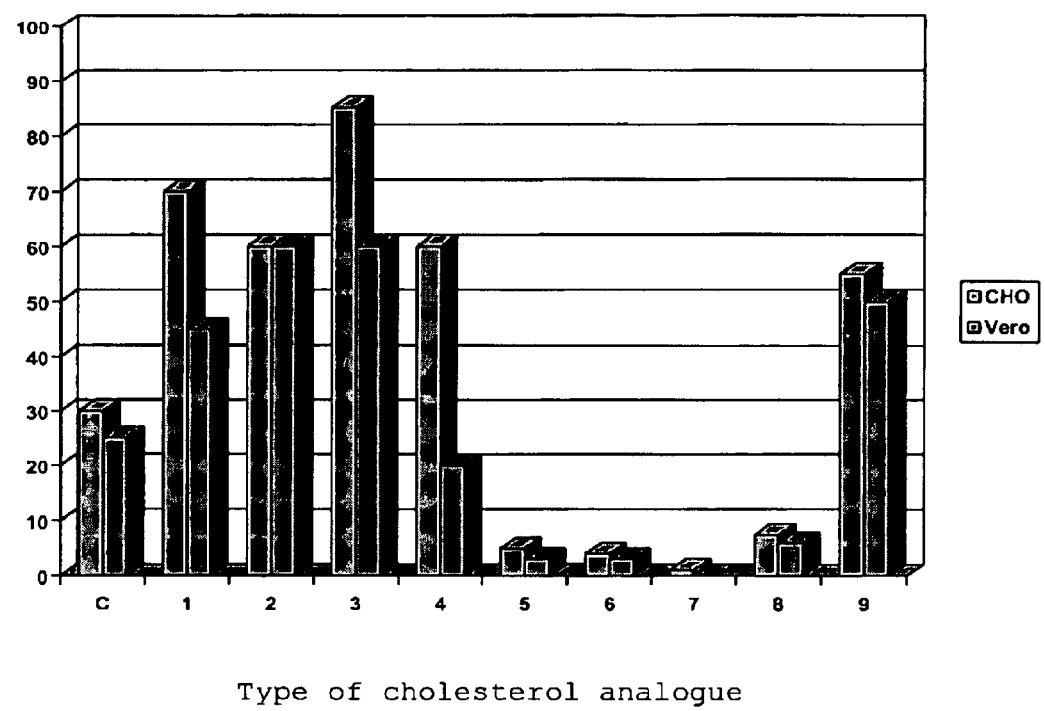
Figure 13:
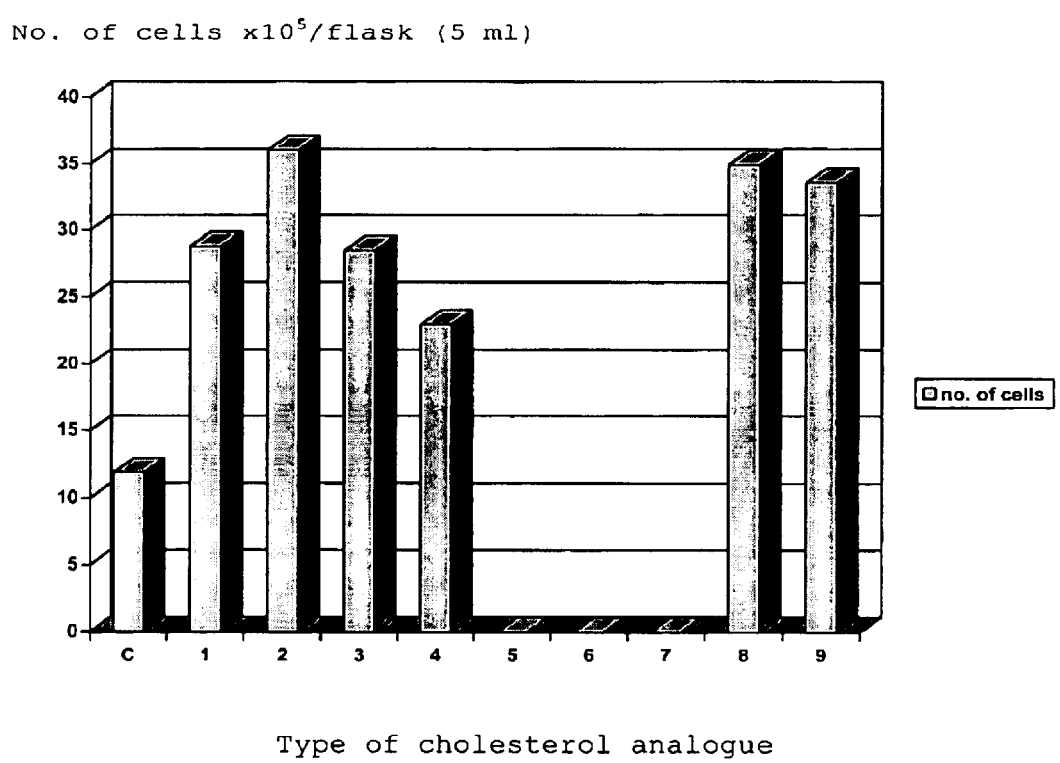

In FIGS. 11 to 13, the legend to the type of cholesterol analogue is as follows:

| 1 Cholesterol | 6 Lanosterol 50–60% |
|---|---|
| 2 Cholesteryl Acetate | 7 Ergocalciferol |
| 3 β-sitosteryl Acetate | 8 β-estradiol |
| 4 Stigmasterol Acetate | 9 Cholic acid |
| 5 7-dehydrocholesterol | C negative control |

The test concentration was 2 μg/ml.

It can be seen that all of the substances tested in the group for which results are shown in FIGS. 8 to 10 are capable of replacing cholesterol in the culture of at least one type of cell. The combination of campesterol and β-sitosterol gave particularly good results, superior to those achieved with cholesterol itself.

The substances for which results are shown in FIGS. 11 to 13 were in general less suitable although good results were obtained with cholesteryl acetate and other sterol acetates and at least in connection with suspended cell culture it appears possible to substitute cholic acid for cholesterol or to benefit sterol containing cultures by the inclusion of cholic acid. Cholic acid is an ionic surfactant and may benefit suspension cultures through the lowering of surface tension it produces.

The optimum sterol for cell culture should meet the following specifications: a) be stable against precipitation in medium at 37° C., b) stimulate cell growth and viability as well as does cholesterol, or better, and c) for adherent cells: produce a high surface tension in the medium for optimum adherence of the cells to the surface by hydrophobic forces.

The sterols which best meet these specifications are:

mixture of 60% β-sitosterol and 40% Campesterol (plant origin/soy bean)

Cholesteryl Acetate (derived from animal)

Campesterol (plant origin/soy bean)

Stigmasterol (plant origin/soy bean)

The β-sitosterol/campesterol mixture (60/40) would probably be the best option for general cell culture. Pure β-sitosterol functions well as a stimulant of cell growth and viability, however, it's stability in medium is less than satisfactory—a property which is strongly improved upon by mixing it with Campesterol.

Other sterols can be used, though less stimulatory effects would be obtained. Cholic acid alone gives a low surface tension of the medium; thus it could be of value in suspension cell culture. A hormone like β-estradiol may stimulate certain cells. Cholesterol itself is somewhat unstable in media; however it can be made stable in solution by modifying the molecule through the introduction of an acetate ester. It's growth-promoting effect is barely affected by this modification. Other sterols may also be modified in this way for use in cell cultures. Cholesteryl Acetate would be the sterol of choice when a physiologically correct environment for human or animal cells is of crucial importance; possibly this might be the case for example in (human) in vitro fertilization, in culture of skin transplants (keratinocytes) and in culture of bone marrow cells.

The 'natural mixture' 60% β-sitosterol (Sigma S 5753) contains to 40% two isomeric forms of Ergost-5-en-3-ol (24-Methyl-cholesterol): 1) Campesterol (3β,24R) and 2) Dihydro-brassicasterol (3β,24S). Both these may be used as cholesterol analogues. Alternative names for some of the sterols discussed above are:

1) Campesterol=24α-Methylcholesterol.

2) Dihydro-brassicasterol=24β-Methylcholesterol.

EXAMPLE 9

The Acceptability of Soluble Organic Acids as Lipid Precursors

As shown above in connection with acetic acid, soluble organic acids may act as precursors of fatty acids necessary for cell growth. In cell culture they may therefore replace water-insoluble fatty acids normally supplied in complexes with serum albumen.

The following substances were tested:

| A 6283 | Acetic acid |
|---|---|
| B 2503 | Butyric acid |
| C 2250 | Caproic acid |
| P 5561 | Propionic acid |
| V 0125 | Valeric acid |

Cells were cultured as described in Example 8 except that as basal medium DME/MCDB 110 was used as DME/F12 contains one fatty acid, namely linoleic acid. Instead of sterols, various fatty acids were added as test substances.

Figure 14:
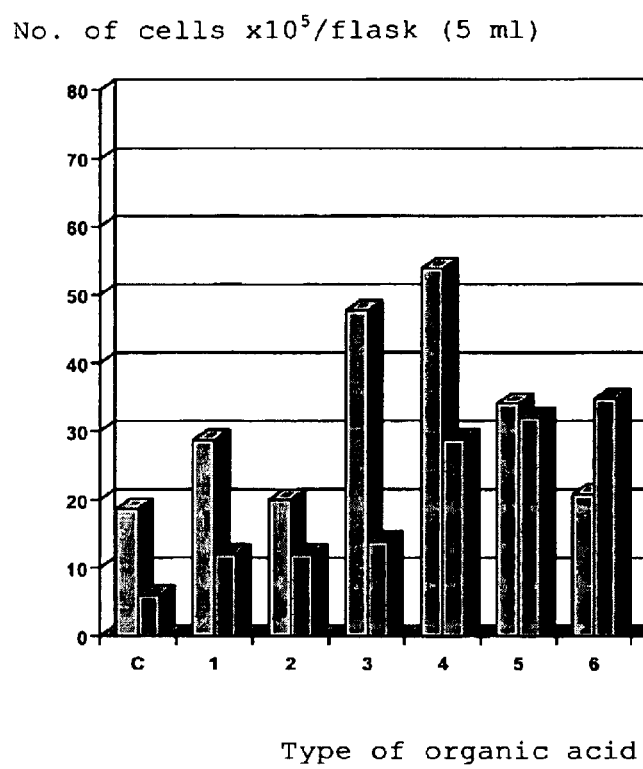
FIGS. 14 to 16 show results obtained in Example 9.
Figure 15:
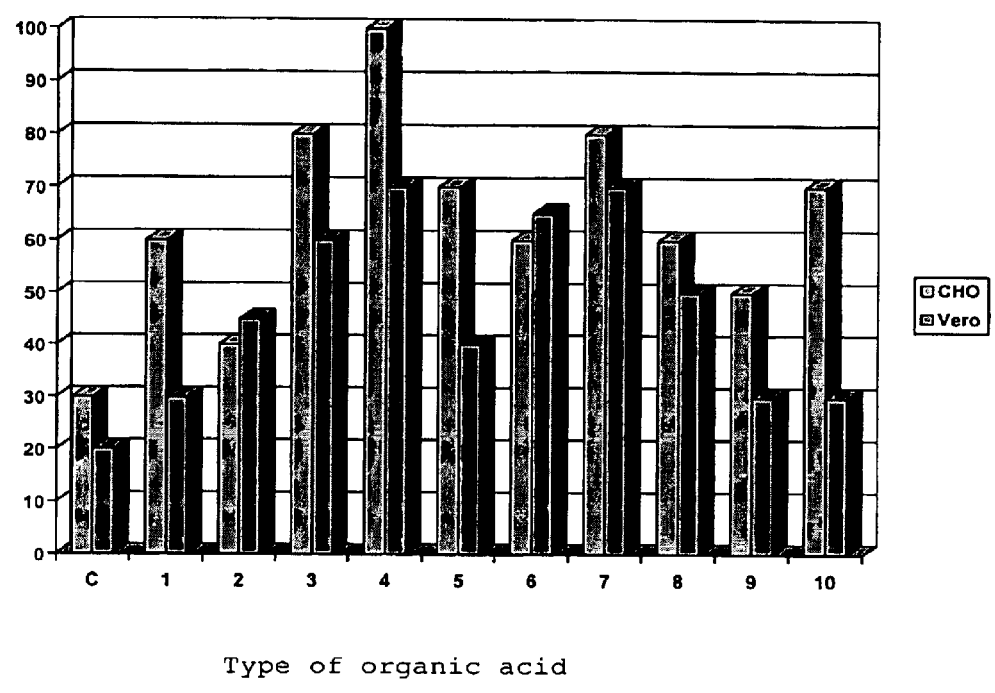
Figure 16:
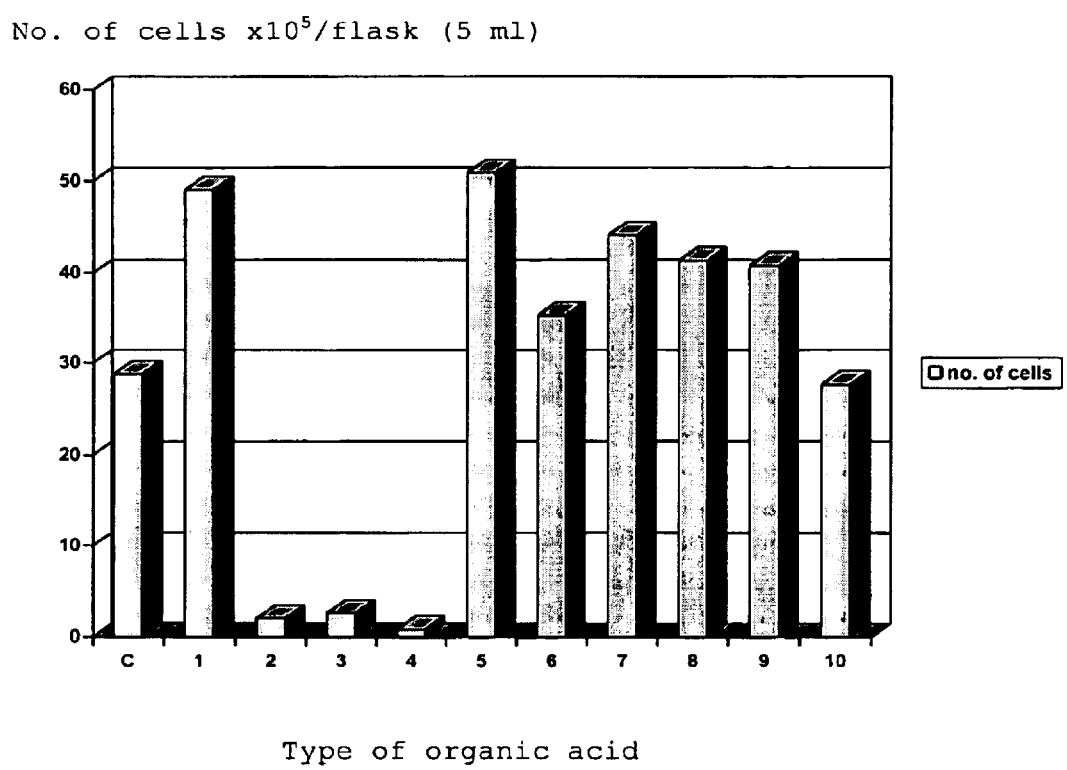

The results are shown in FIGS. 14 to 16. The legend for the type of organic acid tested in these figures is:

| 1 Acetic acid 1x | 7 Propionic acid 1x |
|---|---|
| 2 Acetic acid 10x | 8 Propionic acid 10x |
| 3 Butyric acid 1x | 9 Valeric acid 1x |

-continued

| 4 Butyric acid 10x | 10 Valeric acid 10x |
| 5 Caproic acid 1x | C negative control |
| 6 Caproic acid 10x | |

Test concentration: 1x = 0.1 mM, or 10x = 1 mM.
For Caproic acid: 0.075 or 0.75 mM.

All organic acids tested could stimulate cell growth and/or viability. A general conclusion then is that any water-soluble carboxylic acid can be used for cell culture. The most important organic acids were (besides acetic acid): propionic acid (0.1 mM), butyric acid (0.1–1 mM) and caproic acid (optimum is probably around 0.2 mM).

For CHO cells butyric acid yields high cell number and good adherence. Propionic acid combines even more rapid growth with development of micro aggregates (special symmetrical cell aggregates) when cultures reach confluence a property of possible importance for future developments in CHO suspension cultures. For Vero cells, propionic acid yields the best results, then caproic acid. For Hybridoma 1E6 the best results were obtained with acetic acid and caproic acid, then propionic acid. Butyric acid inhibits growth. However, viability of the cultured cells is good, and the possibility exists that butyric acid may stimulate cellular production processes by reducing the growth rate.

EXAMPLE 10
The Growth Stimulating Effect of Alcohols

Cell culture was again carried out as described in Example 8, but with the addition of a number of alcohols rather than sterols. We suspect that increased solubility of water-insoluble material obtained through the addition of alcohols aids cellular transport processes and the content and distribution of membrane-associated molecules in cultured cells (including lateral mobility: 'membrane fluidity').

The following substances were tested:

| | |
|---|---|
| E 9129 | Ethanol |
| | Ethylene Glycol |
| G 2025 | Glycerol |
| 27,067–9 | 1-Butanol |
| 29,328–8 | 1-Propanol |

Figure 17:
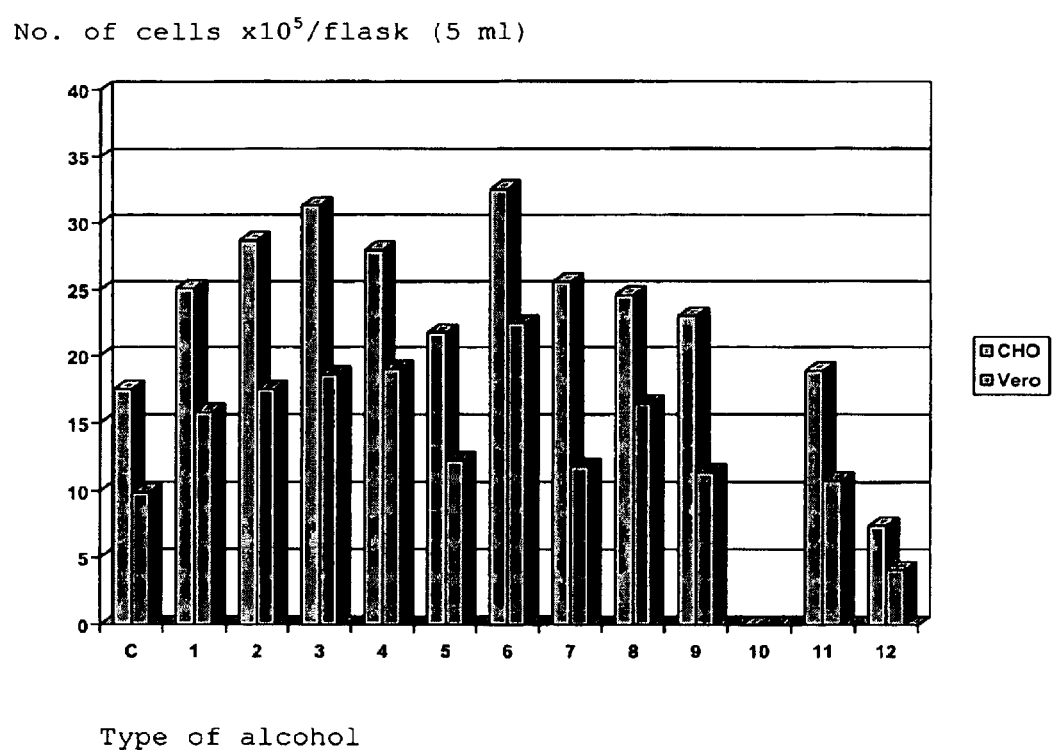
FIGS. 17 and 18 show result obtained in Example 10.
Figure 18:
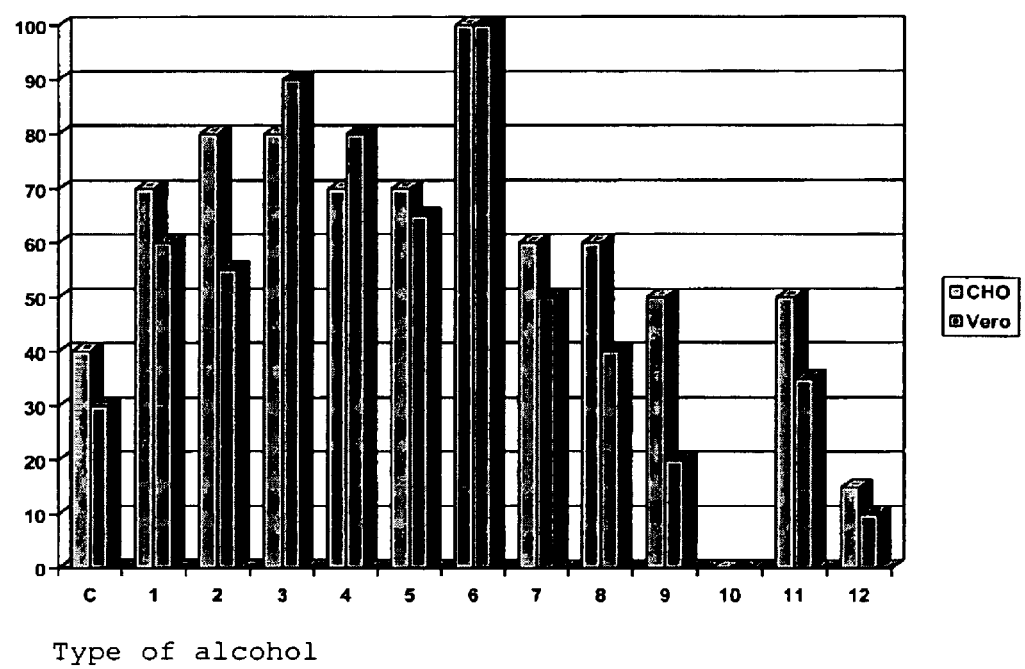

Ethanol and Methanol were tested and compared in Example 1 where both showed similar positive effects on cell growth for hybridoma cells in protein-free medium. The results obtained in the present example in adherent cell culture are shown in FIGS. 17 and 18. The legend to the identification of the alcohols tested in these figures is as follows:

List of alcohols:

| 1 | Ethanol 1x | 7 | Glycerol 1x |
| 2 | Ethanol 5x | 8 | Glycerol 5x |
| 3 | Ethylene Glycol 1x | 9 | 1-Butanol 1x |
| 4 | Ethylene Glycol 5x | 10 | 1-Butanol 5x |
| 5 | Propylene Glycerol 1x | 11 | 1-Propanol 1x |
| 6 | Propylene Glycerol 5x | 12 | 1-Propanol 5x |
| | | C | negative control |

Test concentration: 1x = 0.1%, or 5x = 0.5%.

The results indicate that for adherent cells ethanol, ethylene glycol and propylene glycol show positive effects on cell growth and viability at concentrations around 0.1%, as earlier found for ethanol and methanol using 1E6 cells in Hybritest. Butanol is toxic at higher concentrations. Generally, at an appropriate concentration, all of the alcohols tested were capable of promoting growth compared to the negative control but none showed as good a result as ethanol at higher concentrations.

EXAMPLE 11
In Vitro Fertilisation

Universal IVF medium is in widespread use for successful IVF treatment. It consists of 10 mg/ml HSA and solution SSR2 described above, plus basal medium. It has not previously proved possible to replace the HSA even though this is highly desirable. We have now compared the use of the said Universal IVF medium with a medium according to this invention, namely one in which instead of HSA and SSR2 the medium contains SSR4x as described above. In trials in which 133 embryo's were cultured the percentage reaching the blastocyst stage were 75% for the Universal IVF medium and 77% for the medium according to the invention. Thus, the invention has provided a viable alternative to the use of serum containing media for use in IVF.

EXAMPLE 12
Protein Expression

A transfected BHK cell line expressing hIL-2 was cultivated in a FCS containing medium and in SSR4x. In separate studies, differing cultivation apparatus was employed, i.e. T-flask, Roller bottles, miniPERM and a continuous perfusion culture system. Similar studies were undertaken using CHO cells transfected for expression of t-PA and for expression of Rubella capsid protein using T-flasks, Spinner flasks, miniPERM and Hollow Fiber System cultivation. Furthermore, the viability of cells frozen in SSR4x was compared to that obtained using an FCS containing medium.

Figure 19:
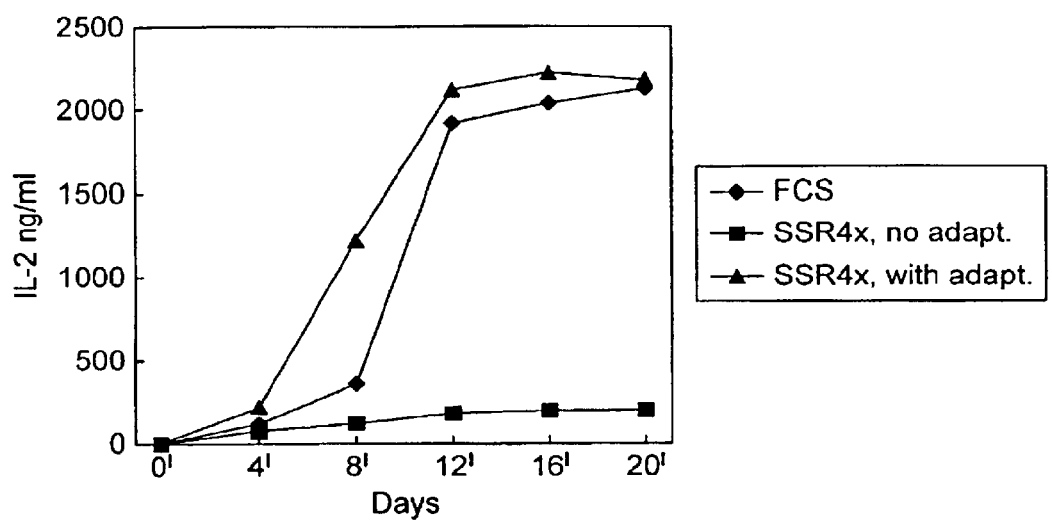
FIG. 19 shows protein expression measured in Example 11.

It was found that for the BHK cells, growth curves were similar for the two media while equal or higher production yields were obtained. In some cases, yields were spectacularly higher. FIG. 19 shows production data for BHK cells expressing human IL-2 in medium supplemented with FCS compared to solution SSR4x described above in a mini PERM Bioreactor (Hereus) system with and without an adaption procedure from FCS to SSR4x cultivation.

For the CHO cells, good growth and production were obtained.

For the freezing tests, it was found that the viability of the cells frozen in the medium of the invention was good and that after 7–8 days the cell numbers were similar to those grown and frozen in the conventional medium. Furthermore, the time for re-establishing cell division on thawing is less than 48 hours, as required by industrial users.

Whilst the invention has been described and illustrated with reference to preferred embodiments thereof, it will be appreciated that many variations and modifications of the preferred aspects of the invention as described above are possible within the general scope of the invention.

What is claimed is:

1. An additive for addition to a basal cell culture medium to form a serum-free cell culture medium, said additive comprising: ethanol as solvent, a carboxylic acid which is soluble in basal cell culture medium and acts as a metabolic precursor of lipid fatty acids, and a sterol component constituting the entire sterol content of the additive and consisting of campesterol an β-sitosterol.

2. An additive for addition to a basal cell culture medium to form a serum-free cell culture medium as claimed in claim 1, wherein said soluble carboxylic acid is a $C_2$ to $C_7$ carboxylic acid.

3. An additive for a cell culture medium as claimed in claim 2, wherein said carboxylic acid is acetic acid.

4. An additive for a cell culture medium as claimed in any one of claims 1 to 3, further comprising: ethanolamine and PVP-10.

5. An additive as claimed in claim 4, wherein said additive contains said ethanolamine and PVP-10 in the proportions 250 g PVP-10:1.2 ml pure, concentrated ethanolamine.

6. An additive as claimed in claim 5, containing ethanol, sterol and acetic acid substantially in the proportions 1 1 96% ethanol:2 g sterol:100 mmols acetic acid.

* * * * *